(12) United States Patent
Cosmescu

(10) Patent No.: US 10,299,849 B2
(45) Date of Patent: May 28, 2019

(54) ARGON BEAM ASSISTED ELECTROSURGERY PENCIL WITH SMOKE EVACUATION

(71) Applicant: I.C. Medical, Inc., Phoenix, AZ (US)

(72) Inventor: Ioan Cosmescu, Phoenix, AZ (US)

(73) Assignee: I.C. Medical, Inc., Phoenix, AZ (US)

(*) Notice: Subject to any disclaimer, the term of this patent is extended or adjusted under 35 U.S.C. 154(b) by 809 days.

(21) Appl. No.: 14/198,877

(22) Filed: Mar. 6, 2014

(65) Prior Publication Data

US 2014/0257273 A1    Sep. 11, 2014

Related U.S. Application Data

(60) Provisional application No. 61/773,239, filed on Mar. 6, 2013.

(51) Int. Cl.
*A61B 18/04* (2006.01)
*A61B 18/00* (2006.01)

(52) U.S. Cl.
CPC .. *A61B 18/042* (2013.01); *A61B 2018/00607* (2013.01); *A61B 2018/00916* (2013.01); *A61B 2218/008* (2013.01)

(58) Field of Classification Search
CPC .................................................. A61B 18/042
See application file for complete search history.

(56) References Cited

U.S. PATENT DOCUMENTS

| 6,458,125 | B1 | 10/2002 | Cosmescu |
| 2005/0113825 | A1 | 5/2005 | Cosmescu |

FOREIGN PATENT DOCUMENTS

| GB | 2406793 A | 4/2005 |
| WO | 2004/026150 A2 | 4/2004 |
| WO | 2005/046498 A1 | 5/2005 |
| WO | 2012/061535 A2 | 5/2012 |

OTHER PUBLICATIONS

International Search Report and Written Opinion from related PCT Application No. PCT/US2014/021127 dated Jul. 7, 2014.

*Primary Examiner* — Daniel W Fowler
(74) *Attorney, Agent, or Firm* — Zeman-Mullen & Ford, LLP

(57) ABSTRACT

A surgical pencil that enables simultaneous cutting with an electrode and coagulating with a coagulating material while also performing smoke evacuation.

20 Claims, 3 Drawing Sheets

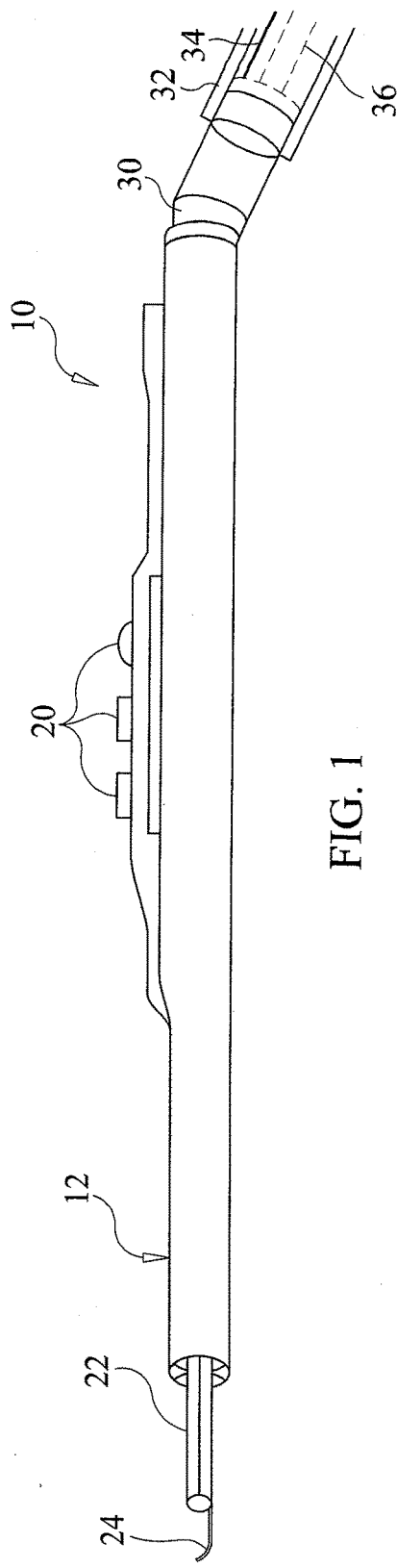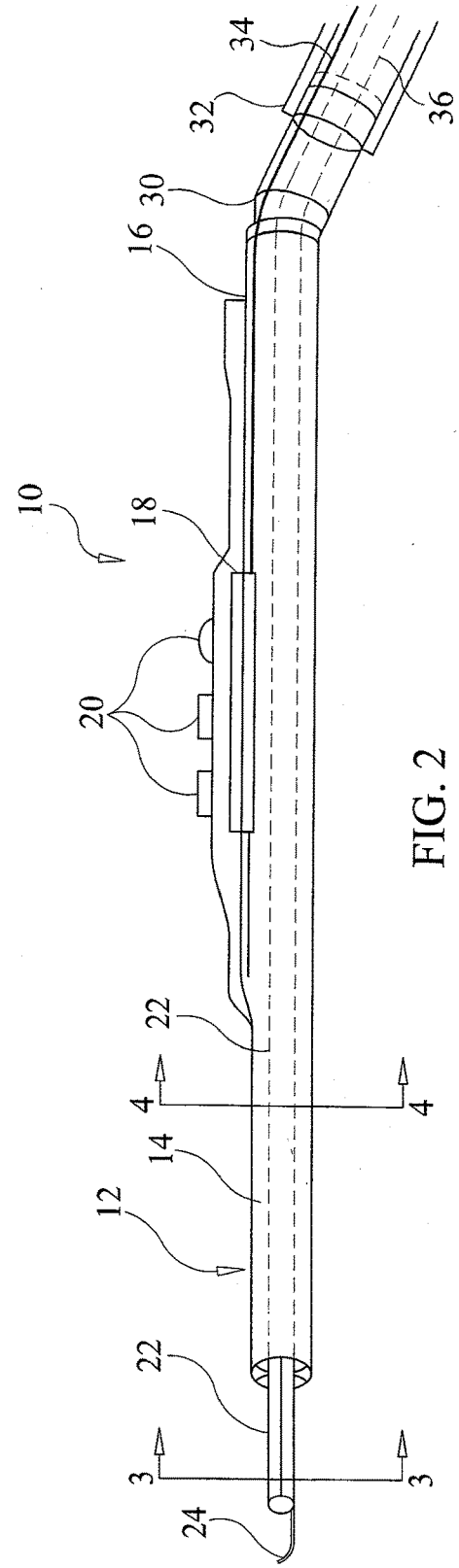

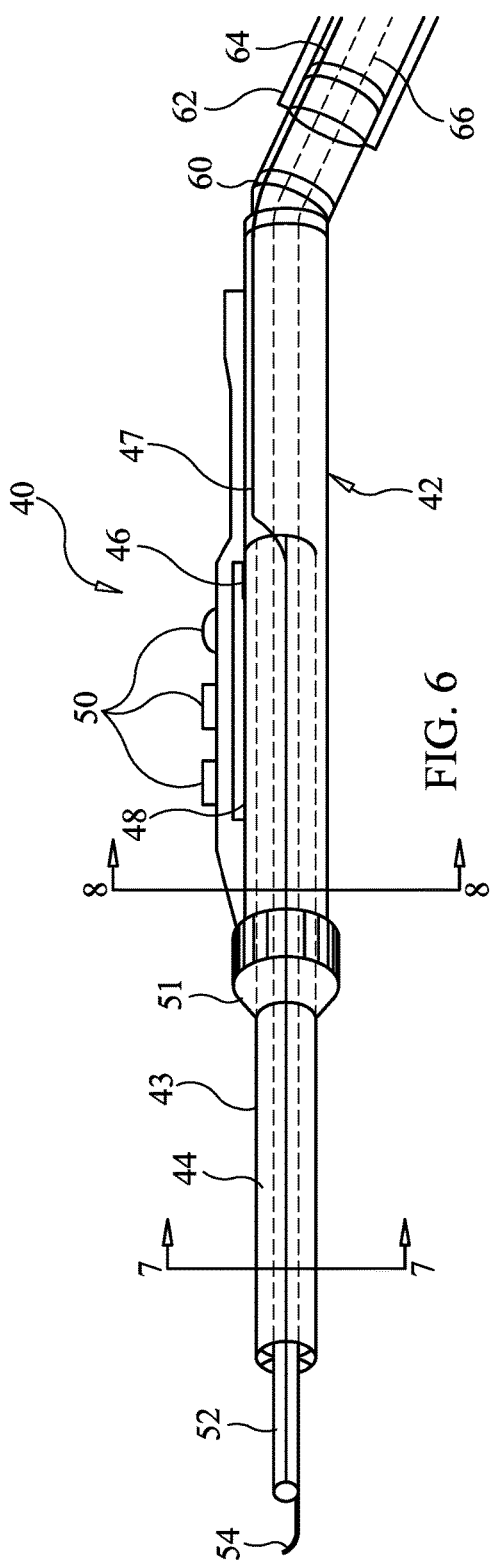
FIG. 6
FIG. 7
FIG. 8

ARGON BEAM ASSISTED ELECTROSURGERY PENCIL WITH SMOKE EVACUATION

CROSS-REFERENCE TO RELATED APPLICATIONS

This application claims priority to provisional patent application having Ser. No. 61/773,239, filed Mar. 6, 2013, which is herein incorporated by reference in its entirety.

FIELD OF INVENTION

The present invention generally relates to an argon beam assisted electrosurgery pencil/handpiece with smoke evacuation that includes the use of argon plasma coagulation in combination with electrosurgery in addition to smoke evacuation. More particularly, the surgical handpiece of the present invention includes functional elements that enable a surgeon/user to perform both cutting via an electrode and argon beam coagulation via the application of an argon beam, in combination with one another, and further, both of theses in combination with smoke evacuation.

BACKGROUND OF THE INVENTION

Several different sources of energy can be used for both open procedures and laparoscopy including electrosurgery and argon beam coagulation. In argon beam coagulation (ABC), current is applied to tissue by a directed beam of ionized argon gas which causes a uniform and shallow coagulation surface thereby stopping blood loss. Electrosurgery uses a power supply and handpiece with one or more electrodes to provide high frequency, alternating current input at various voltages (200-10,000V) depending on the function, namely coagulation vs. cutting. For cutting, heat generated from continuous low voltage conduction can create a vapor pocket which vaporizes and explodes a small section of tissue which results in an incision. For coagulation, voltage is usually lower than in cut mode and the slower heating process results in less heat. As a result, no vapor pocket is formed so the tissue for the most part remains intact but with cells and vessels destroyed and sealed at the point of contact.

Surgeons typically need to switch between argon beam coagulation and electrosurgery modes depending on what is happening during the surgery and what they need to achieve at a particular point in the surgery such as cutting, or making incisions in tissue, or stopping the bleeding at the surgical site. At present, electrosurgery is often the best method for cutting and argon beam coagulation is often the best method for cessation of bleeding during surgery. However surgical tools and devices currently available to surgeons require switching between these two methods during the surgical procedure.

Accordingly, there is a need for a surgical device or tool that enables a surgeon or user to utilize the best methods used for cutting and cessation of bleeding at the surgical site at the same time, or simultaneously, while also being able to evacuate smoke and debris away form the surgical site. Such a surgical device or tool would enable the surgeon or user to increase both the efficiency and accuracy of the surgery by enabling the surgeon or user to perform both tissue cutting and coagulation at the same time without switching between modes or methods thereby decreasing operating time. In addition, performing both tissue cutting and coagulation at the same time along with smoke evacuation would enable the surgeon or user to more clearly view the surgical site to ensure accuracy during the procedure without the need to stop and switch modes in order to stop bleeding at the surgery site before being able to clearly see the surgical site.

SUMMARY OF THE INVENTION

The present invention is directed to a surgical pencil that enables simultaneous cutting with an electrode and coagulation with a coagulating material while also performing smoke evacuation. In one exemplary embodiment, the surgical pencil of the present invention includes a handpiece having a conduit contained therein and at least one electrical contact, a hollow tubular member concentrically contained within the conduit so that there is a space between the inner circumference of the handpiece and the outer circumference of the hollow tubular member and the electrical contact element is in contact with the hollow tubular member, an electrode connected to the hollow tubular member and to the electrical contact element, means for connecting an energy source to the electrical contact element, means for providing a coagulating material supply to the hollow tubular member, means for effectuating simultaneous cutting with the electrode and coagulation with the coagulating material, and means for supplying a vacuum to the space between the handpiece and the hollow tubular member. The electrode can be positioned such that the coagulating material flows along all sides of, or completely around, the electrode during simultaneous cutting and coagulation. The hollow tubular member may be comprised of a metal and the coagulating material may be argon gas where a direct beam of ionized argon gas is applied to the surgical site during coagulation.

The simultaneous cutting with the electrode and coagulation with ionized argon gas may also be simultaneously carried out while performing smoke evacuation with the vacuum. The end of the hollow tubular member and the end of the electrode connected to the hollow tubular member may preferably extend at least 3 cm beyond the end of the handpiece to ensure that coagulating material, such as argon gas for example, coming out of the hollow tubular member for coagulating is not immediately drawn back into the handpiece while smoke evacuation is taking place.

In another exemplary embodiment, the surgical pencil of the present invention includes a handpiece having a conduit and at least one electrical contact element, a hollow tubular member comprised of a conducting material that is concentrically contained within the conduit such that there is a space between the inner circumference of the handpiece and the outer circumference of the hollow tubular member and at least one electrical contact element in contact with the hollow tubular member, an electrode connected to the hollow tubular member, means for connecting an energy source to the electrical contact element, means for providing a coagulating material supply to the hollow tubular member, and means for supplying a vacuum to the space between the handpiece and the hollow tubular member. The hollow tubular member may be comprised of a metal and the coagulating material may be argon gas where a direct beam of ionized argon gas is applied to the surgical site during coagulation.

The surgical pencil having the hollow tubular member comprised of a conducting material may include means for simultaneously effectuating cutting with the electrode and coagulation with the coagulating material and the electrode may be positioned so that the coagulating material flows along all sides, or completely around, the electrode during simultaneous cutting and coagulation.

The surgical pencil having the hollow tubular member comprised of a conducting material may also include means for simultaneously effectuating the following: cutting with the electrode, coagulating with the coagulating material, and evacuating smoke and/or debris with the vacuum. In this instance, the end of the hollow tubular member and the end of the electrode connected to the hollow tubular member may preferably extend at least 3 cm beyond the end of the handpiece to ensure that argon gas coming out of the hollow tubular member for coagulating is not immediately drawn back into the handpiece while smoke evacuation is taking place.

In yet another exemplary embodiment, the surgical pencil of the present invention is telescopic and includes a handpiece having at least one electrical contact, a telescopic member having a conduit circumferentially positioned within the handpiece for adjusting the length of the telescopic member extending from the handpiece, a hollow tubular member comprised of a conducting material concentrically contained within the conduit of the telescopic member such that there is a space (such as an annular space, for example) between the inner circumference of the telescopic member and the outer diameter of the hollow tubular member where the electrical contact element of the handpiece is in contact with the hollow tubular member, an electrode connected to the hollow tubular member, means for connecting an energy source to the electrical contact element, means for providing a coagulating material supply to the hollow tubular member, and means for supplying a vacuum to the space between the telescopic member and the hollow tubular member.

The surgical pencil having the telescopic member and the hollow tubular member comprised of a conducting material may include means for simultaneously effectuating cutting with the electrode and coagulation with the coagulating material and the electrode may be positioned so that the coagulating material flows along all sides, or completely around, the electrode during simultaneous cutting and coagulation.

The surgical pencil having the telescopic member and the hollow tubular member comprised of a conducting material may also include means for simultaneously effectuating the following: cutting with the electrode, coagulating with the coagulating material, and evacuating smoke and/or debris with the vacuum. In this instance, the end of the hollow tubular member and the end of the electrode connected to the hollow tubular member may preferably extend at least 3 cm beyond the end of the telescopic member to ensure that coagulating material, such as argon gas for example, coming out of the hollow tubular member for coagulating is not immediately drawn back into the telescopic member and the handpiece while smoke evacuation is taking place.

BRIEF DESCRIPTION OF THE DRAWINGS

The subject invention will hereinafter be described in conjunction with the appended drawing figures, wherein like numerals denote like elements, and FIG. 1 is a perspective view of one exemplary embodiment of the argon beam assisted electrosurgery pencil of the present invention;

FIG. 2 is the argon beam assisted electrosurgery pencil shown in FIG. 1 with internal components of the pencil shown in phantom;

FIG. 6 is the telescopic argon beam assisted electrosurgery pencil shown in FIG. 5 with internal components shown in phantom;

FIG. 7 is a cross-sectional view taken along line 7-7 of FIG. 6; and

FIG. 8 is a cross-sectional view taken along line 8-8 of FIG. 6.

DETAILED DESCRIPTION

Figure 4:
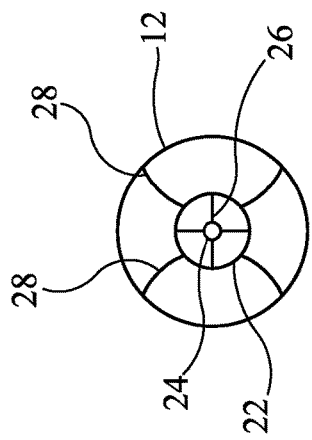
FIG. 4 is a cross-sectional view taken along line 4-4 of FIG. 2.

The argon beam assisted electrosurgery pencil of the present invention generally provides for simultaneous tissue cutting with an electrode and tissue coagulation with a coagulating material while also providing simultaneous evacuation of smoke and debris form the surgical site. FIG. 1 shows a perspective view of an exemplary embodiment of an argon beam assisted electrosurgery pencil 10 in accordance with the present invention while FIG. 2 shows the internal components of the pencil 10 in FIG. 1 in phantom. The exemplary embodiment of the argon beam assisted electrosurgery pencil 10 shown in FIGS. 1 and 2 includes a handpiece 12 having a conduit 14 contained therein and at least one electrical contact 16 which can take one of many forms known by those skilled in the art. Electrical contact 16 is connected to an electrical contact board 18 by way of a wire or similar means where the electrical contact board 18 serves to enable selection and activation of cutting and coagulation via selection buttons 20. Selection buttons 20 may take several forms including separate buttons that can be selected to activate cutting with an electrosurgery blade, coagulation with an electrosurgery blade, and/or coagulation with a coagulating material such as argon gas or, alternatively, election of just one button may activate both cutting with an electrosurgery blade and coagulation with a coagulating material simultaneously without the need to elect two separate buttons.

Figure 3:
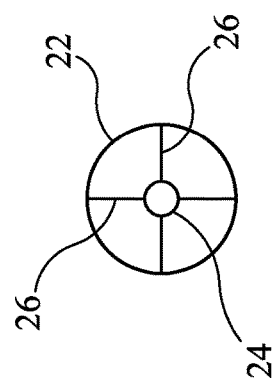
FIG. 3 is a cross-sectional view taken along line 3-3 of FIG. 2.

Argon beam assisted electrosurgery pencil 10 also includes a hollow tubular member 22 concentrically contained within the conduit 14 of handpiece 12 for directing a coagulating material to the surgical site, and an electrode 24 connected to the hollow tubular member 22. In addition, hollow tubular member 22 may be comprised of a conducting material such as a metal and, in this instance, electrode 24 may be connected to any part of hollow tubular member 22 as long as hollow tubular member 22 is connected to electrical contact 16. Alternatively, in another configuration, electrode 24 may be connected to electrical contact 16 by way of a wire or other conducting element that traverses the length of the hollow tubular member 22. Electrode 24 is preferably connected to hollow tubular member 22 by way of spacers 26 shown in FIG. 3 so that electrode 24 is positioned to enable coagulating material directed through hollow tubular member 22 to the surgical site to flow along all sides of, or completely surround, electrode 24. The cross-sectional view of argon beam assisted electrosurgery pencil 10 shown in FIG. 4 shows that spacers 28 are also used to suspend hollow tubular member 22 concentrically within handpiece 12 so that a vacuum can be applied to an end of handpiece 12 opposite electrode 24 in order to evacuate smoke and debris from the surgical site that is created during cutting and coagulation. Accordingly, the hollow tubular member 22 is positioned within handpiece 12 so that a space is created between an inner circumference of the handpiece 12 and an outer circumference of the hollow tubular member 22 thereby enabling a vacuum to be applied to this space.

The exemplary embodiment of the argon beam assisted electrosurgery pencil 10 shown in FIGS. 1 and 2 also shows a swivel device 30 connected to, or incorporated as part of, the evacuation end of pencil 10 which is in turn attached to a vacuum tube 32. Electrical cord 34 which connects electrical contact board 18 to an energy source and hollow tube 36 through which coagulating material is supplied to hollow tubular member 22 are both contained within swivel device 30 to facilitate use of the pencil 10 by the surgeon or user so that the vacuum tube 32 can twist and/or swivel without turning the pencil 10 in the surgeon's hand. Hollow tube 36 may be continuous and the same as, or connected to and separate from, hollow tubular member 22.

Argon beam assisted electrosurgery pencil 10 is capable of simultaneously cutting using electrode 24 and coagulation using coagulating material delivered to the surgical site through hollow tubular member 22 while at the same time also evacuating smoke and/or debris from the surgical site by applying a vacuum to vacuum tube 32. The end of the hollow tubular member 22 and the end of the electrode 24 connected to the hollow tubular member 22 may preferably extend at least 3 cm beyond the end of the handpiece 12 to ensure that coagulating material such as argon gas, for example, coming out of the hollow tubular member 22 for coagulating is not immediately drawn back into the handpiece 12 while smoke evacuation is taking place.

Figure 5:
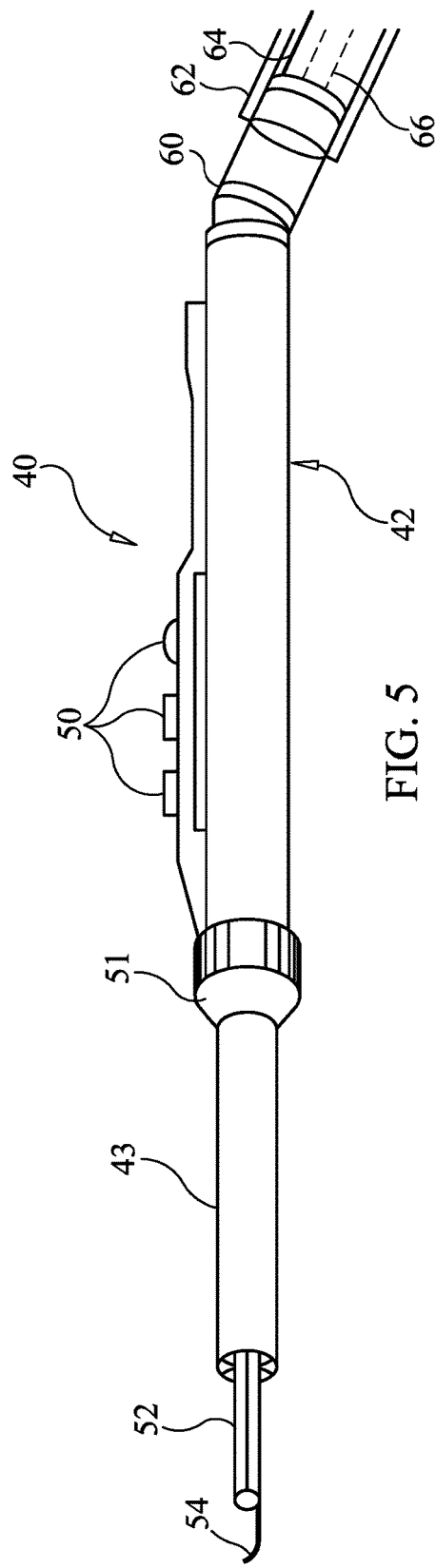
FIG. 5 is a perspective view of another exemplary embodiment of the argon beam assisted electrosurgery pencil of the present invention that is telescopic.

FIG. 5 depicts another exemplary embodiment of an argon beam assisted electrosurgery pencil 40 in accordance with the present invention while FIG. 6 shows the internal components of the pencil 40 in FIG. 5 in phantom. The exemplary embodiment of the argon beam assisted electrosurgery pencil 40 shown in FIGS. 5 and 6 is a telescopic argon beam assisted electrosurgery pencil. The telescopic argon beam assisted electrosurgery pencil 40 shown in FIGS. 5 and 6 includes a handpiece 42 having at least one electrical contact 46, a telescopic member 43 having a conduit 44 therein circumferentially positioned within handpiece 42 for adjusting the length of telescopic member 43 extending from handpiece 42, a hollow tubular member 52 concentrically contained within the conduit 44 so that there is a space between the inner circumference of the telescopic member 43 and the outer circumference of the hollow tubular member 52. The electrical contact element 46 may take many forms including, but not limited to, a cylindrical conducting element lining an interior circumferential surface of the handpiece 42, an elongated electrical contact that is positioned along a length of the interior surface of the handpiece 42, or a contact element that is a small conducting element or piece that is connected to some part of the handpiece 42.

Electrical contact element 46 is connected to an electrical contact board 48 by way of a wire or similar means where the electrical contact board 48 serves to enable selection and activation of cutting and coagulation via selection buttons 50. Selection buttons 50 may take several forms including separate buttons that can be selected to activate cutting with an electrosurgery blade, coagulation with an electrosurgery blade, and/or coagulation with a coagulating material such as argon gas or, alternatively, election of just one button may activate both cutting with an electrosurgery blade and coagulation with a coagulating material simultaneously without the need to elect two separate buttons.

The argon beam assisted electrosurgery pencil 40 also includes an electrode 54 that is ultimately connected to the electrical contact element 46 of the handpiece 42 by one or more connections. For example, the electrode 54 may be connected to the hollow tubular member 52 which is formed from a conducting material and the hollow tubular member 52 may be in turn connected to electrical contact element 46 by a wire 47. In still another example of connecting the electrode 54 to the electrical contact element 46 of the handpiece 42, electrode 54 may be connected to a wire that runs the length of the interior of hollow tubular member 52 which is in turn, connected to a conducting element contained on an outer surface of telescopic member 43 which in turn engages an elongated electrical contact that is positioned along a length of the interior of handpiece 42. These are just some examples of ways to connect electrode 54 to electrical contact element 46 of handpiece 42 and are nor meant to be limiting in any way. Those skilled in the art will recognize that many alternative connection possibilities exist that enable connection of electrode 54 to an electrical contact element contained on any portion of handpiece 42 where such connections may include connections to conducting elements contained on several components of pencil 40 in turn or to conducting elements contained on very few components of pencil 40. The type and complexity of the connections used will depend on the desired configuration of the pencil 40.

Electrode 54 is preferably connected to hollow tubular member 52 by way of spacers 56 shown in FIG. 7 so that electrode 54 is positioned to enable coagulating material directed through hollow tubular member 52 to the surgical site to flow along all sides of, or completely around, electrode 54. The cross-sectional view of argon beam assisted electrosurgery pencil 40 shown in FIG. 7 shows that spacers 58 are also used to suspend hollow tubular member 52 concentrically within telescopic member 43 so that a vacuum can be applied to an end of handpiece 42 opposite electrode 54 in order to evacuate smoke and debris from the surgical site that is created during cutting and coagulation. Accordingly, the hollow tubular member 52 is positioned within telescopic member 43 so that a space is created between an inner circumference of telescopic member 43 and an outer circumference of the hollow tubular member 52 thereby enabling a vacuum to be applied to this space. As depicted in the cross-sectional view shown in FIG. 8, telescopic member 43 is closely circumferentially fit within handpiece 42 so that telescopic member 43 can slide along an interior of handpiece 42 so that it can extend beyond an end of handpiece 42 that is opposite the end of handpiece 42 where a vacuum is applied. A locking member 51 (See FIGS. 5 and 6) may be used to secure telescopic member 43 in place in relation to handpiece 42. This may be done by way of tightening locking member 51 onto telescopic member 43. Examples of such locking members and how they function can be found in the prior art.

The exemplary embodiment of the argon beam assisted electrosurgery pencil 40 shown in FIGS. 5 and 6 also shows a swivel device 60 connected to, or incorporated as part of, the evacuation end of pencil 40 which is in turn attached to a vacuum tube 62. Electrical cord 64 which connects electrical contact board 48 (and thereby electrical contact 46) to an energy source and hollow tube 66 through which coagulating material is supplied to hollow tubular member 52 are both contained within swivel device 60 to facilitate use of the pencil 40 by the surgeon or user so that the vacuum tube 62 can twist and/or swivel without turning the pencil 40 in the surgeon's hand. Hollow tube 66 may be continuous and the same as, or connected to and separate from, hollow tubular member 52.

Argon beam assisted electrosurgery pencil 40 is capable of simultaneously cutting using electrode 54 and coagulation using coagulating material delivered to the surgical site through hollow tubular member 52 while at the same time also evacuating smoke and/or debris from the surgical site by applying a vacuum to vacuum tube 62. The end of the hollow tubular member 52 and the end of the electrode 54 connected to the hollow tubular member 52 may preferably extend at least 3 cm beyond the end of the telescopic member 43 to ensure that coagulating material such as argon gas, for example, coming out of the hollow tubular member 52 for coagulating is not immediately drawn back into the telescopic member 43 and the handpiece 42 while smoke evacuation is taking place.

The detailed description of exemplary embodiments of the invention herein shows various exemplary embodiments of the invention. These exemplary embodiments and modes are described in sufficient detail to enable those skilled in the art to practice the invention and are not intended to limit the scope, applicability, or configuration of the invention in any way. Rather, the following disclosure is intended to teach both the implementation of the exemplary embodiments and modes and any equivalent modes or embodiments that are known or obvious to those reasonably skilled in the art. Additionally, all included examples are non-limiting illustrations of the exemplary embodiments and modes, which similarly avail themselves to any equivalent modes or embodiments that are known or obvious to those reasonably skilled in the art.

Other combinations and/or modifications of structures, arrangements, applications, proportions, elements, materials, or components used in the practice of the instant invention, in addition to those not specifically recited, can be varied or otherwise particularly adapted to specific environments, manufacturing specifications, design parameters, or other operating requirements without departing from the scope of the instant invention and are intended to be included in this disclosure.

Unless specifically noted, it is the Applicant's intent that the words and phrases in the specification and the claims be given the commonly accepted generic meaning or an ordinary and accustomed meaning used by those of ordinary skill in the applicable arts. In the instance where these meanings differ, the words and phrases in the specification and the claims should be given the broadest possible, generic meaning. If any other special meaning is intended for any word or phrase, the specification will clearly state and define the special meaning.

The invention claimed is:

1. A surgical pencil comprising:
   a handpiece having a conduit contained therein and at least one electrical contact element;
   a hollow tubular member comprised of a conducting material wherein said hollow tubular member is concentrically contained within said conduit such that it extends along an entire length of said handpiece and such that there is a space between an inner circumference of said handpiece and an outer circumference of said hollow tubular member along an entire length of said handpiece, and said at least one electrical contact element is in contact with said hollow tubular member;
   an electrode connected to said hollow tubular member;
   means for connecting an energy source to said at least one electrical contact;
   means for providing a coagulating material supply to said hollow tubular member; and
   means for supplying a vacuum to said space between said handpiece and said hollow tubular member.

2. The surgical pencil of claim 1 further comprising a swivel member connected to the handpiece at an end of the handpiece opposite the electrode wherein at least one of a portion of the hollow tubular member and a portion of the means for providing a coagulating material supply to the hollow tubular member are contained within the swivel member.

3. The surgical pencil of claim 1 further comprising means for effectuating simultaneous cutting with the electrode and coagulation with the coagulating material.

4. The surgical pencil of claim 3 wherein the electrode is positioned such that the coagulating material can flow along all sides of said electrode during simultaneous cutting and coagulation.

5. The surgical pencil of claim 1 further comprising means for effectuating simultaneous cutting with the electrode, coagulation with the coagulating material, and smoke evacuation with the vacuum.

6. The surgical pencil of claim 1 wherein the coagulating material is argon gas.

7. The surgical pencil of claim 1 wherein an end of the hollow tubular member and an end of the electrode connected to the hollow tubular member extend at least 3 cm beyond an end of the handpiece.

8. A telescopic surgical pencil comprising:
   a handpiece having at least one electrical contact;
   a telescopic member having a conduit therein circumferentially positioned within the handpiece for adjusting a length of the telescopic member extending from the handpiece;
   a hollow tubular member comprised of a conducting material wherein said hollow tubular member is concentrically contained within said conduit such that it extends along an entire length of said handpiece and such that there is a space between an inner circumference of said telescopic member and an outer circumference of said hollow tubular member along an entire length of said handpiece, and said at least one electrical contact element is in contact with said hollow tubular member;
   an electrode connected to said hollow tubular member;
   means for connecting an energy source to said at least one electrical contact;
   means for providing a coagulating material supply to said hollow tubular member; and
   means for supplying a vacuum to said space between said telescopic member and said hollow tubular member.

9. The surgical pencil of claim 8 further comprising a swivel member connected to the handpiece at an end of the handpiece opposite the electrode wherein at least one of a portion of the hollow tubular member and a portion of the means for providing a coagulating material supply to the hollow tubular member are contained within the swivel member.

10. The surgical pencil of claim 8 further comprising means for effectuating simultaneous cutting with the electrode and coagulation with the coagulating material.

11. The surgical pencil of claim 10 wherein the electrode is positioned such that the coagulating material can flow along all sides of said electrode during simultaneous cutting and coagulation.

12. The surgical pencil of claim 8 further comprising means for effectuating simultaneous cutting with the electrode, coagulation with the coagulating material, and smoke evacuation with the vacuum.

13. The surgical pencil of claim 8 wherein the coagulating material is argon gas.

14. The surgical pencil of claim 8 wherein an end of the hollow tubular member and an end of the electrode connected to the hollow tubular member extend at least 3 cm beyond an end of the telescopic member.

15. A surgical pencil for simultaneous cutting with electrosurgery and coagulation with a coagulation material comprising:
- a handpiece having a conduit contained therein and at least one electrical contact element;
- a hollow tubular member concentrically contained within said conduit such that it extends along an entire length of said handpiece and such that there is a space between an inner circumference of said handpiece and an outer circumference of said hollow tubular member along an entire length of said handpiece and said at least one electrical contact element is in contact with said hollow tubular member;
- an electrode connected to said hollow tubular member and to said at least one electrical contact element;
- means for connecting an energy source to said at least one electrical contact;
- means for providing a coagulating material supply to said hollow tubular member;
- means for effectuating simultaneous cutting with the electrode and coagulation with the coagulating material; and
- means for supplying a vacuum to said space between said handpiece and said hollow tubular member.

16. The surgical pencil of claim 15 wherein the electrode is positioned such that the coagulating material can flow along all sides of said electrode during simultaneous cutting and coagulation.

17. The surgical pencil of claim 15 further comprising a swivel member connected to the handpiece at an end of the handpiece opposite the electrode wherein at least one of a portion of the hollow tubular member and a portion of the means for providing a coagulating material supply to the hollow tubular member are contained within the swivel member.

18. The surgical pencil of claim 15 further comprising means for effectuating simultaneous smoke evacuation with the vacuum during simultaneous cutting and coagulation.

19. The surgical pencil of claim 15 wherein the coagulating material is argon gas.

20. The surgical pencil of claim 15 wherein an end of the hollow tubular member and an end of the electrode connected to the hollow tubular member extend at least 3 cm beyond an end of the handpiece.

* * * * *